(12) United States Patent
Kerr

(10) Patent No.: US 6,945,936 B1
(45) Date of Patent: Sep. 20, 2005

(54) STERILE OPHTHALMIC BARRIER DEVICE

(76) Inventor: Jonathan Quinton Kerr, Bullbeggars, Godstone, Surrey RH9 8BJ (GB)

( * ) Notice: Subject to any disclaimer, the term of this patent is extended or adjusted under 35 U.S.C. 154(b) by 154 days.

(21) Appl. No.: 10/031,538

(22) PCT Filed: Jul. 11, 2000

(86) PCT No.: PCT/GB00/02683

§ 371 (c)(1),
(2), (4) Date: May 10, 2002

(87) PCT Pub. No.: WO01/05299

PCT Pub. Date: Jan. 25, 2001

(30) Foreign Application Priority Data

Jul. 17, 1999  (GB) .................................. 9916743

(51) Int. Cl.⁷ .............................................. A61B 3/16
(52) U.S. Cl. ...................... 600/406; 374/158; 374/209
(58) Field of Search .............................. 600/398–400, 600/402, 405, 406, 489, 549, 561; 150/154; 351/200, 219; 206/69, 461, 484; 374/158, 374/209; 128/897

(56) References Cited

U.S. PATENT DOCUMENTS

| | | | |
|---|---|---|---|
| 4,922,914 A | 5/1990 | Segal et al. | |
| 5,002,057 A | 3/1991 | Brady | |
| 5,113,863 A | 5/1992 | Herman | |
| 5,448,025 A * | 9/1995 | Stark et al. | 181/131 |
| 5,887,590 A * | 3/1999 | Price | 128/858 |
| 5,935,058 A * | 8/1999 | Makita et al. | 600/200 |
| 6,123,454 A * | 9/2000 | Canfield et al. | 374/158 |
| 6,254,386 B1 * | 7/2001 | Ohmes | 433/30 |

FOREIGN PATENT DOCUMENTS

FR          2683990 A      5/1993

OTHER PUBLICATIONS

Nardi M., Bartolomei M.P., Falco L., Carelli F.: "Disposable Film Cover for the Tip of Goldmann's Tonometer"; Graefe's Archive for Clinical and Experimental Ophthalmology, vol. 223, 1985, pp. 109-110, XP000943189.

* cited by examiner

*Primary Examiner*—Charles Marmor
(74) *Attorney, Agent, or Firm*—Lahive & Cockfield, LLP; Anthony A. Laurentano, Esq.

(57) ABSTRACT

A barrier for use in relation to an eye contacting testing apparatus of the sort having a probe for contacting the eye, comprises a layer of substantially transparent material having dimensions comparable to the surface of the head of the probe and is removably fixable to the probe by means, such as a peelable adhesive, which do not affect the transparency of the material layer. The layer is sterile on the surface which contacts the eye in place of the probe head. Such barriers are disposable and quick and easy to position and replace. Barriers according to the invention can be conveniently provided in sheets comprising multiples of barriers.

9 Claims, 3 Drawing Sheets

STERILE OPHTHALMIC BARRIER DEVICE

This invention relates to ophthalmic apparatus used in the testing and diagnosis of various eyesight defects and eye disorders. In particular the invention relates to such apparatus which come into contact with the patient's eye and to improved prevention of transfer of infection between eyes tested using the apparatus.

The diagnosis of certain eye conditions often requires the oculist to measure certain properties of the eye. Often, the measurement of such properties is most accurately and simply achieved by the use of instruments which contact the cornea of the eye. The most common of these procedures is the Goldman Applanation Tonometry test which is used in the routine measurement of intraocular pressure. Other contact procedures include scan biometry for measuring the axial length of the eye prior to cataract surgery. Another example of a contact procedure is spectral endothelial microscopy which is used to assess the health of the corneal endothelial cells. Similar, but less common procedures include: transillumination used to view the inside of the eye, pachometry used for measuring corneal thickness and gonioscopy used to examine the anterior chamber of the eye.

It is known that various disease-causing microbes can be carried in the tears. Examples of diseases which may be transmitted through the tears include Herpes Simplex, Adenovirus, conjunctivitis, the HIV virus and prions such as that which may cause Creuzvelt Jacob Disease (CJD). Thus there is an infection risk associated with the various contact procedures involving instruments touching the cornea of the eye.

Conventionally the apparatus used in the diagnosis of eye conditions is sterilised by the use of a chemical sterilising agent (eg an alcohol such as surgical spirit) often provided in the form of a medi-swab or a surgical wipe. Such sterilising agents, if allowed to come into contact with the cornea of the eye, can cause chemical burns which, as the eye is anaesthetised during the test procedure, are often not detected until some time later. In order to prevent damage to the eye, the sterilising agent must either be allowed to evaporate, this can take up to three minutes for each application, or may be washed off with saline solution or alternatively wiped with a dry tissue. When the sterilising agent is allowed to evaporate, this considerably increases the time taken to perform a simple ophthalmic test. Consequently, the sterilising procedure is not always performed when transferring from one eye of a patient to the other and this may result in cross contamination between the eyes of a patient. When dry tissues or saline are used to remove the residual sterilising agent, there is a potential risk that the unsterile tissues and saline may themselves transfer a contaminant to the surface of the ophthalmic apparatus and into the eye of the patient.

A further disadvantage of the conventional sterilising techniques is that the chemical sterilising agents used often do not destroy certain microbial contaminants known to be carried in the tears. One example of such a microbe is the Adenovirus.

As an alternative, a number of sterile barriers have been developed to shield the eye from the surface of the ophthalmic apparatus. These barriers generally take the form of sterile, transparent plastic caps or sheaths which can be positioned over the contacting surface of the ophthalmic apparatus each time a new patient is examined. These barriers may be re-sterilised before re-use or may be discarded and replaced with fresh barriers.

Examples of cap-type barriers are described in U.S. Pat. Nos. 4,922,914, 5,282,470 and 5,031,622. An example of a sheath-type barrier is described in U.S. Pat. No. 5,002,057. Whilst these prior art devices no doubt provide protection against the transmission of disease-causing microbes between patients, they are relatively costly to manufacture and cumbersome to package in bulk. Practitioners in eye units may see dozens of patients in a week and may find these bulky and costly barriers unattractive or not cost effective as a disposable option.

It is an object of the present invention to provide a simple, low cost solution to the problems associated with conventional methods of sterilising ophthalmic apparatus.

In accordance with the present invention there is provided a barrier for use in relation to an eye contacting optical testing apparatus, the apparatus having a probe for contacting the eye, the barrier comprising a layer of substantially transparent material having dimensions comparable to the surface of the head of the probe and being removably fixable to the probe by means which do not affect the transparency of the material layer and the layer being sterile on at least one of its surfaces.

The material may be any transparent material which is relatively inert in a saline or aqueous environment. Preferred materials include polymers such as polyethylene.

Various fixing means may be used to releasably fix the barrier to the probe of the optical apparatus. For example a peelable or pressure sensitive adhesive may be applied to one surface of the barrier, or alternatively to tabs which affix to the side rather than the head of the probe. Preferably, an adhesive is water-based, optionally it comprises a hydrogel. Alternatively a suitable material may be chosen such that it will cling by means of static or surface tension to the head of the probe.

The barrier may conveniently be provided in the form of a laminate comprising a central layer of optically transparent material having applied to one surface a layer of adhesive material and optionally, a layer of sterilising agent applied to the other. The transparent material may, of course, be sterilised by other means and the barrier provided with just the transparent and adhesive layer.

Suitable barrier materials and adhesives can be found from the prior art in the field of biomedical engineering. Some examples of suitable barrier materials include, but are not limited to: polyesters, polycarbonates, polyamides, ethylene vinyl acetate copolymer, polyvinyl chloride and its copolymers, polysulphones, cellulose acetate and other cellulose derivatives. Examples of suitable adhesives include but are not limited to: rubber-based adhesives, acrylic adhesives and modified acrylic adhesives, silicone based adhesives and hydrogel and hydrocolloid adhesives.

Preferably, the perimeter of the barrier will in at least one radial direction, extend beyond that of the head of the probe. This provides tabs which can be wrapped over the edge of the probe head where tears may accumulate when a patient blinks during examination, thereby further reducing the risk of cross-infection. Various geometric arrangements can be envisaged to provide these wrap-over tabs on a barrier adapted to fit a typically round probe head of an optical apparatus. Some examples of suitable geometries include a tear drop shape, a square with sides approximately equal to the diameter of the probe head wherein the corners of the square can be used to remove the barrier, or a triangle whose apexes can be wrapped over the edges of the probe.

In another option the barrier may be substantially circular in shape with one or more protruding square or rectangular tabs about its circumference. Other suitable geometries include: a flower shaped design consisting of a circular area which is approximately the same diameter as the probe head with a plurality of arcuate or conical petals which can be folded over the side or collar of the probe head. Preferably the tabs will adhere to the edges of the probe head.

Optionally the tabs may be in part non-adherent to the probe head and can be used to aid removal of the barrier after use. For example, in the case of the flower shaped design, one of the petals may extend further than the others to provide a tag which will be non-adhesive for easy removal of the barrier after use. Alternatively one or more of the petals may be non-adhesive, there being sufficient adherent petals remaining to cover substantially all of the head and collar of the probe.

Preferably, the tabs of a barrier extend to cover at least about 5 mm of the side/collar of the probe head.

In an alternative form, the barrier may be manufactured from a material having slightly elastic properties. The barrier is then supplied as a flat sheet but can be stretched over the end of the probe head and released to grip the edges the probe head.

In order to facilitate easy location of the barrier on the probe head one or more coloured markers or indicators may be provided to define the edge of the barrier or the edge of the probe head on which it is to be placed.

Optionally this marker or indicator may be provided in the form of a coloured ring which is provided to be of a size coincident with the outer perimeter of the probe head. In this case the barrier can be located on the probe head simply by aligning the coloured ring with the perimeter of the probe head. In addition to providing a simple means of locating the barrier on the probe head, the colour indicator may also provide an indication as to which surface of the barrier is sterile where only one surface is sterile. It should be understood that a series of two or more displaced dots, lines or arcs may equally be used to define the area of the probe head.

It will be understood from the preceding description of the barrier of the present invention that such a barrier can be provided relatively inexpensively. Whilst it may be possible to re-sterilise the barrier, it is preferred that the barrier is provided in packs of sheets comprising a multitude of such barriers and that the barriers are used only for a single application and are then disposed of.

In another aspect the invention provides a sheet comprising a number of pieces of substantially transparent material, the pieces having dimensions substantially similar to those of the probe head of an eye contacting optical apparatus, the material being sterile on at least the surface which will contact the eye.

The sheet can conveniently be manufactured using a roll-to-roll coating process where the adhesive and/or sterile layer is applied to the barrier material in a sheet-like form. Individual barriers can then be cut or pressed from the resulting laminate. Backing sheets may be added before or after the individual barriers are cut from the sheet.

Preferably the sheet is provided with a backing sheet from which it is peelable. Optionally one surface may be provided with a peelable adhesive, which may also be provided with a backing sheet.

Thus it can be seen that a multitude of disposable ophthalmic barriers according to the present invention can be provided in the convenient form of a sheet provided between two backing sheets. By peeling away one backing sheet the user can reveal the adhesive surface of a barrier, and can position this on the probe head. Once the barrier is located on the probe head, the second backing sheet or a portion thereof can be peeled away revealing the sterile surface. Thus, the sterility of the sterile surface of the barrier is maintained until the barrier contacts the eye under test. The provision of tabs or protrusions as previously described, allows for quick and simple removal of a barrier such that a fresh barrier can be applied before the second eye of the patient or a subsequent patient is tested.

Optionally, the backing sheet adjacent the sterile surface of the barrier may be provided with a coloured marker indicating the outer perimeter of the barrier or of the probe head. This can be provided as an alternative or in addition to the markers previously described in association with the barrier itself. Again, the marker is used by the oculist to align the barrier with the perimeter of the probe head. Preferably the coloured marker is provided in the form of a coloured ring designed to be coincident with the outer perimeter of the probe head. Optionally the non-sterile surface of the sheet of barriers may be provided without an adhesive; in such a case, an adhesive may be applied separately. Alternatively, an adhesive surface may be provided, in a form whereby its adhesive property is dependant on the provision of a separate ingredient such as water. An example of such an adhesive may be found on the conventional postage stamp.

Optionally the sheet with its backing sheets may be provided with perforations by which the oculist can remove a strip comprising any pre-desired number of barriers. Optionally the perforations may be arranged to define individual barriers or pairs of barriers.

For the purposes of exemplification the invention may be further described with reference to the Figures in which:—

Figure 1:
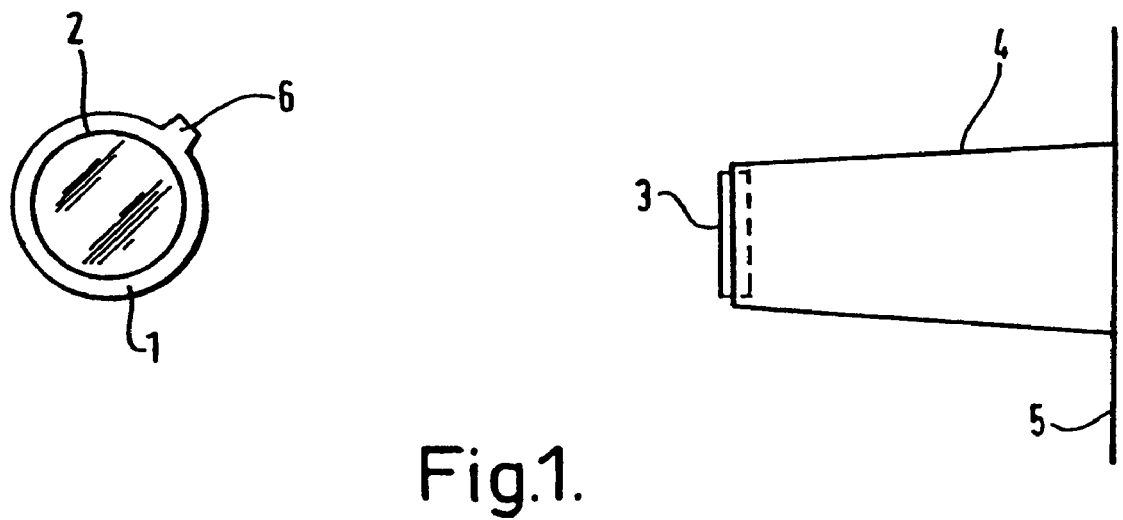
FIG. 1 shows a first embodiment of a barrier according to the present invention.

In FIG. 1 a barrier 1 comprising a substantially circular piece of transparent material is provided with a coloured ring-shaped marker 2 of comparable size to the perimeter of a probe head 3 located on a probe 4 of a piece of optical apparatus 5. The ring 2 is of comparable dimension to the perimeter of the probe head 3. The barrier 1 is also provided with a protruding tab 6 which can be used as a means of levering the barrier from the probe head once used.

Figure 2:
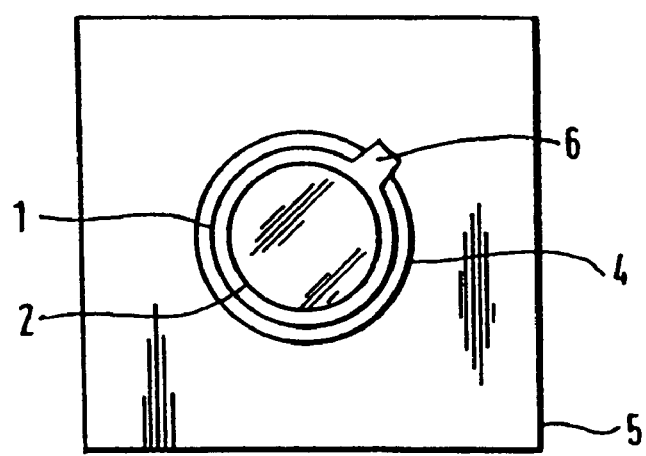
FIG. 2 shows the embodiment of FIG. 1 located on a typical probe head of some optical apparatus.

FIG. 2 shows the embodiment of FIG. 1 arranged on the probe head. As can been seen from the Figure the coloured ring 2 is positioned coincident with the perimeter of the probe head 3. The protruding tab 6 does not communicate with the surface of the probe head 3 and thus can be easily held and pulled to remove the barrier once used. In the embodiments of FIG. 1 or 2 the surface of the barrier adjacent the probe is provided with some form of adhering means.

Figure 3:
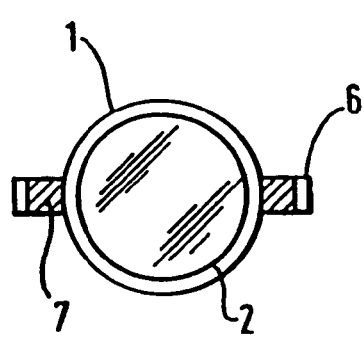
FIG. 3 shows a second embodiment of the invention.
Figure 3:
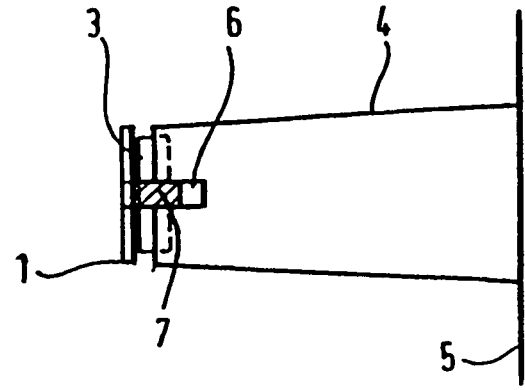

In FIG. 3 an alternative embodiment of the barrier 1 is provided with two protruding tabs 6 on which is provided a patch of adhesive material 7. Once the barrier is located on the probe head by means of colour marking 2, the adhesive tabs 6 are fixed against the sides of the probe 4 to hold the barrier into position.

Figure 4A:
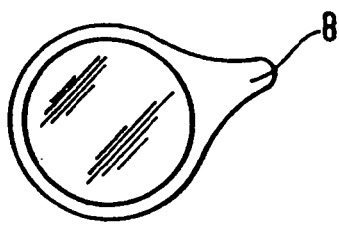
FIG. 4 shows three alternative embodiments of the invention.
Figure 4B:
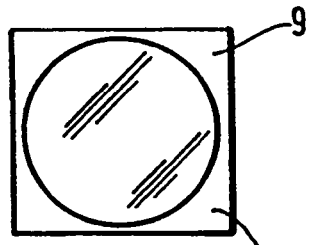
Figure 4C:
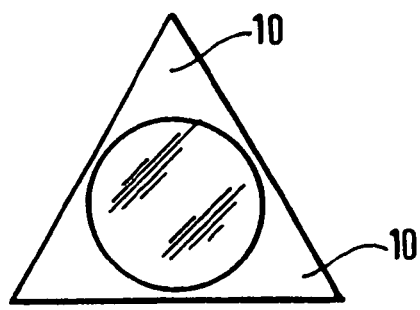

FIG. 4 shows some alternative shapes for the barrier. FIG. 4a shows a teardrop-shaped barrier of which the apex 8 features as a convenient tab to aid removal of the barrier following use. Similarly FIG. 4b shows a square shaped barrier of which the corners 9 can be used to provide a tab to aid removal of the barrier following use. Again similarly in FIG. 4c a triangular barrier is provided of which the apexes 10 provide a convenient tab means to aid removal.

Figure 5:
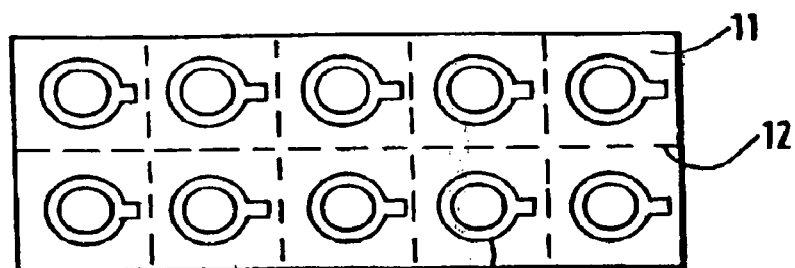
FIG. 5 shows a sheet of barriers according to the present invention.

FIG. 5 shows a backing sheet 11 on which are arranged a multitude of barriers 1 according to the invention. The sheet 11 is perforated by perforation lines 12 to enable the user to tear off strips or individual barriers to facilitate easier location of an individual barrier.

Figure 6:
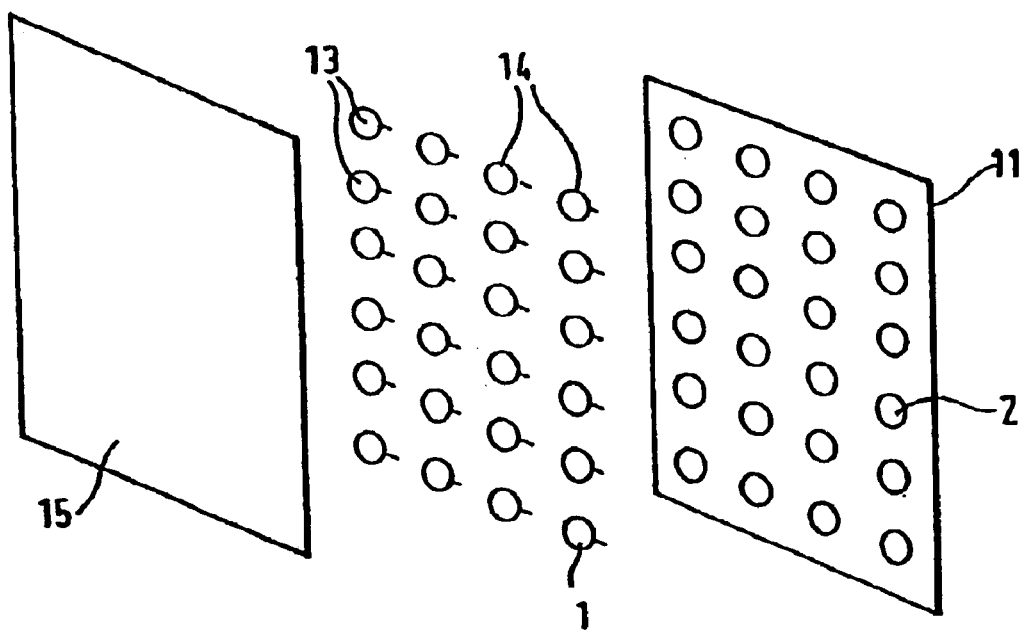
FIG. 6 shows a layout of some barriers according to the present invention with associated backing sheets.

FIG. 6 shows the layout of another alternative embodiment according to the present invention. In FIG. 6 a backing sheet 11 is provided with a multitude of coloured rings 2 having dimensions comparable to the perimeter of a typical probe head 3 of an optical apparatus 5. A multitude of barriers 1 having sterile surfaces 14 and surfaces provided with peelable adhesive 13 are arranged on backing sheet 11 in positions coincident with the colour marker rings 2. A second backing sheet 15 is provided to protect the peelable adhesive surface.

Figure 7:
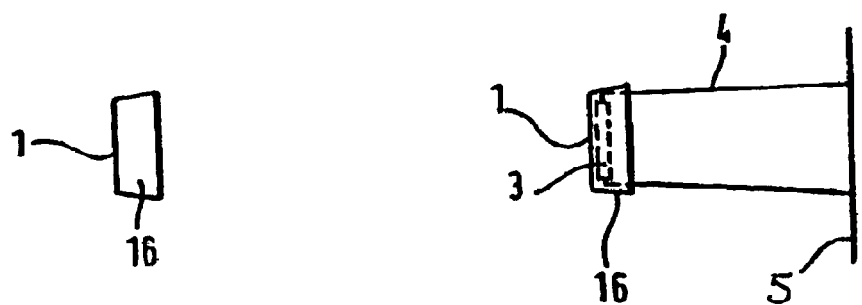
FIG. 7 shows another alternative embodiment of the present invention.

FIG. 7 shows another alternative embodiment of the invention. A barrier 1 according to the present invention is provided with a collar 16, the collar being of such a size as to provide a friction fit with the walls of the probe 4 which carry probe head 3 of optical apparatus 5. It will be understood that it is not essential for collar 16 to have a friction fit if the barrier is provided with some form of gripping collar (not shown) to hold the collar 16 in position on the head of the probe 4.

The embodiments described in FIGS. 1 to 7 are just some alternative examples of the invention and are not intended to be limiting.

The skilled reader will understand that in order to maintain accuracy of the optical instruments, the surface of the barrier placed over the probe head should be parallel to and in very close communication with the optical surface of the probe head.

The barriers of the present invention hereinbefore described may be used with any optical device having a probe head designed to make contact with the eye. Examples of such optical devices include, but are not limited to; Goldman tonometer heads, Gonioscope lenses, 3-mirror Goldman and other diagnostic contact lenses, A-scan ultrasound probes, YAG laser lenses, retinal laser lenses, vitrectomy lenses, ultrasound pachometry apparatus, trans-illumination apparatus and dynamometers.

What is claimed is:

1. A pack of barriers for use in relation to an eye contacting optical testing apparatus, comprising a first backing sheet on which are removably attached a plurality of barriers of substantially transparent film each having dimensions comparable to those of an eye-contacting surface of a head of a probe of the optical testing apparatus, a surface of the substantially transparent film adjacent the first backing sheet being sterile and the alternative surface of the substantially transparent film being provided with a peelable adhesive, and a second backing sheet to which the plurality of barriers and the first backing sheet are adhered by the peelable adhesive, wherein the first backing sheet is provided with locating means for locating the head of the probe of the optical testing apparatus.

2. A pack of barriers as claimed in claim 1 wherein the locating means comprises coloured markers.

3. A pack of barriers as claimed in claim 2 wherein the locating means comprises a series of coloured rings each ring having a perimeter substantially coincident with that of the head of the probe of the optical testing apparatus.

4. A pack of barriers as claimed in claim 1 wherein the first backing sheet is provided with weakened lines to enable a portion of the first backing sheet surrounding one or more barriers to be removed by tearing of the first backing sheet along the weakened lines.

5. A pack of barriers as claimed in claim 4 wherein the weakened lines are provided in the form of perforations.

6. A pack of barriers as claimed in claim 1 wherein each barrier is provided with one or more tabs for easy removal of the barrier.

7. A pack of barriers as claimed in claim 6 wherein the tabs are provided with an adhesive substance for retaining the barrier onto the head of the probe.

8. A sheet of barriers for use in relation to an eye contacting optical apparatus comprising a plurality of pieces of substantially transparent material removably attached to a backing sheet, the pieces having dimensions substantially similar to those of a probe head of the eye contacting optical apparatus, the pieces having at least one sterile surface being in contact with the backing sheet, wherein the backing sheet is removed from each piece to reveal the sterile surface and the backing sheet is provided with locating means for locating the head of the probe of the optical testing apparatus.

9. A sheet of barriers as claimed in claim 8 wherein a surface of each piece of substantially transparent material is provided with a peelable adhesive.

* * * * *